US010436916B2

(12) United States Patent
Freiburger et al.

(10) Patent No.: US 10,436,916 B2
(45) Date of Patent: Oct. 8, 2019

(54) MODULE SYSTEM FOR A RADIOMETRIC MEASURING DEVICE

(71) Applicant: BERTHOLD TECHNOLOGIES GmbH & Co. KG, Bad Wildbad (DE)

(72) Inventors: Ewald Freiburger, Neulingen (DE); Tobias Daibenzeiher, Neuenbuerg (DE)

(73) Assignee: Berthold Technologies GmbH & Co. KG, Bad Wildbad (DE)

( * ) Notice: Subject to any disclaimer, the term of this patent is extended or adjusted under 35 U.S.C. 154(b) by 0 days.

(21) Appl. No.: 15/854,988

(22) Filed: Dec. 27, 2017

(65) Prior Publication Data

US 2018/0203135 A1    Jul. 19, 2018

(30) Foreign Application Priority Data

Jan. 13, 2017    (EP) .................................... 17151496

(51) Int. Cl.
*G01T 1/20*    (2006.01)
*G01T 1/175*    (2006.01)
(Continued)

(52) U.S. Cl.
CPC .......... *G01T 1/2018* (2013.01); *G01F 23/288* (2013.01); *G01T 1/175* (2013.01);
(Continued)

(58) Field of Classification Search
CPC ......... G01T 1/20; G01T 1/202; G01T 1/2023; G01T 1/2002; G21K 4/00
See application file for complete search history.

(56) References Cited

U.S. PATENT DOCUMENTS 6,366,436 B1    4/2002    Maier et al.
2007/0273542 A1    11/2007    Mellert et al.
(Continued)

FOREIGN PATENT DOCUMENTS

DE    299 15 862 U1    1/2001
EP    0 945 714 A1    9/1999
(Continued)

OTHER PUBLICATIONS

Bertero, "An Arduino'd Radiation Meter—Now That's a Radiant Idea," Elektor Post, Project No. 6, dated May 3, 2013, with English translation, pp. 1-3, XP 55389640A (Six (6) pages).

*Primary Examiner* — David P Porta
*Assistant Examiner* — Mamadou Faye
(74) *Attorney, Agent, or Firm* — Crowell & Moring LLP

(57) ABSTRACT

A module system for a radiometric measuring device includes a basic module having a sensor arrangement designed to generate a measurement signal on the basis of radiation which strikes the sensor arrangement, a signal evaluation unit electrically coupled to the sensor arrangement and being designed to determine a measurement variable on the basis of the measurement signal, a control device interface, wherein the basic module is coupleable to at least one control device by the control device interface for interchanging data, the basic module being supplied with electrical energy solely via its control device interface in a basic operating state, and an expansion module interface. The module system further includes an expansion module which is separate from the basic module and has a basic module interface, the basic module interface being able to be coupled to the expansion module interface for interchanging data, interchanging energy, and/or interchanging measurement signals, a number of functional groups, and an energy supply interface coupleable to an energy supply unit separate from the basic module and the expansion module, (Continued)

wherein energy provided via the energy supply interface is used to supply energy to the expansion module.

11 Claims, 1 Drawing Sheet

(51) Int. Cl.
  G01F 23/288 (2006.01)
  G01T 3/06 (2006.01)
  G01T 3/08 (2006.01)
  G01N 9/36 (2006.01)
  G01N 23/09 (2018.01)
(52) U.S. Cl.
  CPC .................. G01T 3/06 (2013.01); G01T 3/08 (2013.01); *G01F 23/2885* (2013.01); *G01N 9/36* (2013.01); *G01N 23/09* (2013.01); *G01N 2223/505* (2013.01)

(56) References Cited

U.S. PATENT DOCUMENTS

| | | | |
|---|---|---|---|
| 2010/0140480 A1* | 6/2010 | Rauer | G01F 23/288 250/357.1 |
| 2010/0252739 A1* | 10/2010 | Damm | G01F 23/288 250/357.1 |
| 2012/0043466 A1* | 2/2012 | Weidenbruch | G01F 23/288 250/362 |
| 2016/0320498 A1* | 11/2016 | Benz | G01T 1/2018 |

FOREIGN PATENT DOCUMENTS

| | | |
|---|---|---|
| WO | WO 2005/075944 A1 | 8/2005 |
| WO | WO 2006/185028 A1 | 11/2016 |

* cited by examiner

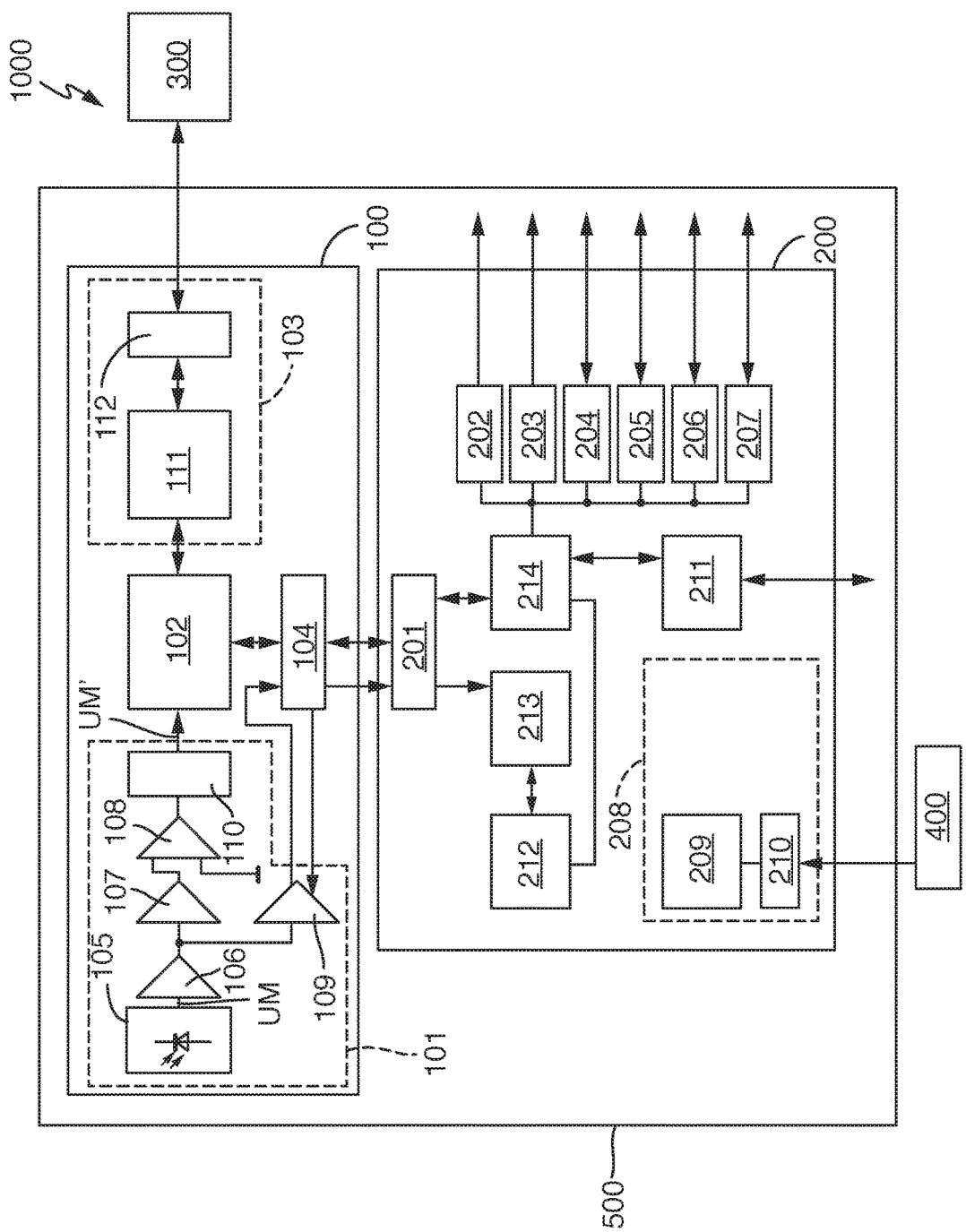

MODULE SYSTEM FOR A RADIOMETRIC MEASURING DEVICE

BACKGROUND AND SUMMARY OF THE INVENTION

The invention relates to a module system for a radiometric measuring device.

The invention is based on the object of providing a module system for a radiometric measuring device, which module system can be used as flexibly as possible.

The invention achieves this object by providing a module system for a radiometric measuring device having a basic module including a sensor arrangement which is designed to generate a measurement signal on the basis of radiation which strikes the sensor arrangement, a signal evaluation unit which is electrically coupled to the sensor arrangement and is designed to determine a measurement variable on the basis of the measurement signal, a control device interface, and an expansion module interface. The basic module is able to be coupled to at least one control device by the control device interface for the purpose of interchanging data. The basic module is designed to be supplied with electrical energy solely via its control device interface in a basic operating state. The module system further has an expansion module which is separate from the basic module and includes a basic module interface, the basic module interface being able to be coupled to the expansion module interface for the purpose of interchanging data, interchanging energy and/or interchanging measurement signals, a number of functional groups, and an energy supply interface which is coupleable to an energy supply unit separate from the basic module and the expansion module, energy provided via the energy supply interface being used to supply energy to the expansion module.

The radiometric measuring device may be, for example, a radiometric scintillation detector for detecting gamma or neutron radiation for measuring the filling level or density in the process industry.

The module system has a basic module.

The basic module has a sensor arrangement which is designed to generate a measurement signal, for example an analog or digital measurement signal, on the basis of radiation, for example gamma or neutron radiation, which strikes the sensor arrangement. The measurement signal may be an analog pulse sequence, for example.

The basic module also has a signal evaluation unit, for example in the form of a microprocessor, which is electrically coupled to the sensor arrangement and is designed to determine a measurement variable on the basis of the measurement signal. For example, the signal evaluation unit may determine a number of pulses of the measurement signal per unit time and may calculate the measurement variable on the basis thereof.

The basic module also has a control device interface, the basic module being able to be coupled to at least one control device by means of the control device interface for the purpose of interchanging data, for example for the purpose of transmitting the measurement variable. The basic module is supplied with electrical energy solely via its control device interface in a basic operating state. The basic operating state is typically that operating state of the radiometric measuring device in which the radiometric measuring device has only the basic module and does not have an expansion module.

The basic module also has an expansion module interface which is typically separate from the control device interface.

The module system also has at least one expansion module which is separate from the basic module. The basic module may be implemented on a first printed circuit board, for example, and the expansion module may be implemented on a second printed circuit board different from the first printed circuit board.

The expansion module has a basic module interface, the basic module interface being able to be coupled to the expansion module interface for the purpose of interchanging data and/or interchanging energy and/or interchanging measurement signals.

The expansion module also has a number, for example between 1 and 10, of functional groups. The functional groups may be embodied in hardware and/or software, for example.

The expansion module also has an energy supply interface which can be coupled to an energy supply unit separate from the basic module and the expansion module. The energy provided by means of the energy supply interface is used to supply energy to the expansion module. The energy provided by means of the energy supply interface can furthermore also be used to (additionally) supply energy to the basic module.

The radiometric measuring device is composed of the basic module and, if functionally necessary, one or more expansion modules.

The functional groups may have an input and/or output functional group, for example in the form of I/O ports, and/or a current output functional group and/or a current input functional group and/or a field bus functional group and/or a tacho signal functional group.

The sensor arrangement may have one or more semiconductor sensor elements which is/are designed to generate the measurement signal on the basis of the radiation, possibly with the aid of suitable analog and/or digital signal conditioning. The semiconductor sensor element may be a semiconductor photodiode with internal amplification, for example an avalanche photodiode (APD) and/or a silicon photomultiplier (SiPM).

The sensor arrangement may have a scintillator and a detector optically coupled to the scintillator, the detector being designed to generate the measurement signal, possibly with the aid of suitable analog and/or digital signal conditioning. The scintillator may be arranged outside a measuring device housing, for example separated from an optical detector by means of a pane of glass or an epoxy resin potting. It goes without saying that the scintillator may also be arranged inside the measuring device housing.

The module system may have a housing, at least the basic module typically being arranged in the housing. If an expanded range of functions of the measuring device is required, the expansion module is additionally arranged in the same housing.

The basic module may have a basic module range of functions, the expansion module(s) or its/their functional groups supplementing and/or expanding the basic module range of functions. For example, the basic module range of functions may comprise only the recording of the measurement variable, but the functional groups provide further functions, for example digital signal processing of the measurement signal.

The expansion module interface, the control device interface and/or the basic module interface may have a safety limitation circuit. The safety limitation circuit may be an Ex i limitation circuit for limiting current, voltage and power. The Ex i limitation circuit has the property of blocking electrical energy contained or stored in the measuring device in the event of a fault or converting it into heat, with the result that it is not passed to the connection terminals of the measuring device and can cause an ignitable mixture to explode. With respect to the configuration of the limitation circuits, reference is made to the relevant technical literature.

The energy provided via the energy supply interface of the expansion module can (also) be used to supply energy to the expansion module interface of the basic module. For example, an interface driver of the expansion module interface of the basic module can be supplied with energy by the expansion module, thus enabling communication between the basic module and the expansion module.

Modular expandability of the radiometric measuring device is possible, if necessary, by means of the module system according to the invention for a radiometric measuring device, for example in the form of a scintillation detector.

The basic module typically has the following elements.

A semiconductor sensor element for directly detecting gamma or neutron radiation or alternatively a scintillator with a semiconductor or vacuum electron multiplier sensor element connected downstream for the purpose of indirectly detecting the secondary radiation (scintillation light) is first of all provided.

Means for analog signal processing are typically also provided in the basic module.

A digital unit of the basic module is then used, for example, to determine a filling level, a density and/or a mass flow from the preprocessed analog signal.

A process interface of the basic module is used for process variable communication.

The basic module can now be expanded and adapted according to customer requirements by coupling one or more expansion modules to the basic module depending on customer requirements.

The basic module can be supplied by means of its process connection. In this case, the basic module may be in the form of a so-called loop-powered field device and/or explosion-proof field device, for example.

With its functions, the basic module covers a predominant portion of the typical requirements. If further functions are additionally required, for example relays, active current outputs, inputs, spectroscopy etc., the basic module is expanded with one or more expansion modules. This makes it possible to achieve the functionality of modern four-wire devices. In addition, functions such as complex digital signal processing can be implemented if necessary.

Since the energy supply for the basic module via its process connection is very limited, an independent energy supply is provided in the expansion module(s), that is to say the two-wire device is upgraded to a four-wire device.

The sensor system of the basic module can be expanded, by means of the functional groups of the expansion module, for the purpose of determining additional parameters relevant to the process variables. Functional groups may record, for example, a process temperature by means of a suitable temperature sensor or 4-20 mA input and/or may record an item of gas density compensation information via a 4-20 mA or field bus interface. Furthermore, a master/slave connection may be provided for the purpose of expanding the measurement range.

If the basic module interface is coupled to the expansion module interface for the purpose of transmitting the measurement signal, the measurement signal can be digitally processed in the expansion module, for example by subjecting the measurement signal to A/D conversion and then digital signal processing. For example, spectral information relating to the detector can therefore be determined. The analog signals for ADC sampling which are required for this purpose can be generated via a driver which is arranged in the basic module and is supplied with energy by the expansion module. This makes it possible to use the high-frequency measurement signal in the expansion module. In a manner derived from the digitized measurement signal or analog signal, it is possible to implement extraneous radiation detection and multi-isotope applications, as are used in analysis systems.

Since considerably more electrical power is available in the expansion module than in the basic module, a multiplicity of different interfaces may be provided on the expansion module, for example current IN/OUT (also in the source mode), pulse IN/OUT, for example for tacho inputs for belt speeds, Ethernet interfaces for field bus protocols, etc.

The independent energy supply for the expansion module makes it possible to operate the measuring device with an input voltage of 20-260 VAC/DC. The energy supply for the expansion module may be designed to be intrinsically safe, for example via a commercially available Ex limitation circuit. As a result, more energy is then made available to the system than by means of the 4-20 mA interface.

It is also possible to supply the expansion module using a supply interface with a superimposed FSK signal.

Other objects, advantages and novel features of the present invention will become apparent from the following detailed description of one or more preferred embodiments when considered in conjunction with the accompanying drawing.

BRIEF DESCRIPTION OF THE DRAWING

FIG. 1 is a block diagram of a module system for a radiometric measuring device having a basic module and an expansion module according to an embodiment of the invention.

DETAILED DESCRIPTION OF THE DRAWING

FIG. 1 shows a block diagram of a module system for a radiometric measuring device 1000. The radiometric measuring device 1000 is illustrated in an exemplary expansion stage in FIG. 1.

The module system or the radiometric measuring device 1000 has a basic module 100. The basic module 100 has a sensor arrangement 101 which is designed to generate a conditioned analog or quasi-digital measurement signal UM' on the basis of radiation which strikes the sensor arrangement 101.

The sensor arrangement 101 has a semiconductor sensor element 105 which is designed to generate a measurement signal UM on the basis of the radiation. Components 106 to 109 for analog signal conditioning, for example for amplifying, filtering etc. the measurement signal UM, are connected downstream of the semiconductor sensor element 105. A comparator 110 of the sensor arrangement 101 finally generates the conditioned measurement signal UM', which is dependent on the measurement signal UM, in the form of a pulse sequence, the counting rate of which is correlated with an intensity of the radiation to be measured. In this respect, reference is also made to the relevant technical literature.

The basic module 100 also has a signal evaluation unit 102 in the form of a microprocessor which is electrically coupled to the sensor arrangement 101 and determines a measurement variable, for example in the form of a filling level, on the basis of the conditioned measurement signal UM'. In this respect, reference is also made to the relevant technical literature.

The basic module 100 also has a control device interface 103 having a 4-20 mA Highway Addressable Remote Transducer (HART) 111 and an Ex i limitation circuit 112. The basic module 100 can be coupled to at least one control device 300 by means of the control device interface 103 for the purpose of interchanging data, the basic module 100 being supplied with electrical energy solely via its control device interface 103 in a basic operating state. The basic module 100 assumes its basic operating state when an expansion module 200 is not coupled to it.

The basic module 100 also has an expansion module interface 104 having an Ex i limitation circuit.

The module system or the radiometric measuring device 1000 also has the optional expansion module 200.

The expansion module 200 has a basic module interface 201 having an Ex i limitation circuit, the basic module interface 201 being coupled to the expansion module interface 104 for the purpose of interchanging data and/or interchanging energy and/or interchanging measurement signals.

The expansion module 200 also has functional groups in the form of an input/output functional group 207, a current output functional group 202, a current input functional group 203, a field bus functional group (RS485 and/or Ethernet) 205, 206 and a tacho signal functional group 204.

The expansion module 200 also has an energy supply interface 208 which can be coupled to an energy supply unit 400 separate from the basic module 100 and the expansion module 200, energy provided via the energy supply interface 208 being able to be used to supply energy to the expansion module 200 and the basic module 100 as long as the expansion module 200 and the energy supply unit 400 are present. The energy supply interface 208 has, by way of example, a power supply unit 209 with a wide input voltage range and an optional Ex i limitation circuit 210.

The expansion module 200 also has an A/D converter 213 in order to digitize the measurement signal UM which is transmitted via the interfaces 104 and 201.

The expansion module 200 also has an optional FPGA 212 which subjects the digitized measurement signal to digital signal processing in order to implement evaluation of the measurement signal UM which goes beyond the rudimentary generation of measured values in the basic module 100.

The expansion module 200 also has a powerful CPU 214 which is designed to provide complex evaluation functions etc. The CPU 214 is coupled to a serial interface 211, for example a USB interface, with the result that results of the evaluation can be transmitted to the outside via the USB interface 211 in the event of maintenance or servicing.

All or some of the components described above are arranged in a housing 500.

As an alternative to the illustration shown, the sensor arrangement may have a scintillator (not illustrated in any more detail) and a detector optically coupled to the scintillator, the detector being designed to generate the measurement signal UM.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A module system for a radiometric measuring device, the module system comprising:
   (a) a basic module that includes
      (i) a sensor arrangement which is designed to generate a measurement signal on the basis of radiation which strikes the sensor arrangement,
      (ii) a signal evaluation unit which is electrically coupled to the sensor arrangement and is designed to determine a measurement variable on the basis of the measurement signal,
      (iii) a control device interface, the basic module being able to be coupled to at least one control device by the control device interface for the purpose of interchanging data, the basic module being designed to be supplied with electrical energy solely via its control device interface in a basic operating state, and
      (iv) an expansion module interface that is separate from the control device interface; and
   (b) an expansion module which is separate from the basic module and includes
      (i) a basic module interface, the basic module interface being able to be coupled to the expansion module interface for the purpose of interchanging data, interchanging energy and/or interchanging measurement signals,
      (ii) a number of functional groups, and
      (iii) an energy supply interface which is coupleable to an energy supply unit separate from the basic module and the expansion module, energy provided via the energy supply interface being used to supply energy to the expansion module.

2. The module system as claimed in claim 1, wherein the number of functional groups includes:
   an input/output functional group, a current output functional group, a current input functional group, a field bus functional group, and/or a tacho signal functional group.

3. The module system as claimed in claim 1, wherein the sensor arrangement has a semiconductor sensor element which is designed to generate the measurement signal on the basis of the radiation.

4. The module system as claimed in claim 1, wherein the sensor arrangement has a scintillator and a detector optically coupled to the scintillator, the detector being designed to generate the measurement signal.

5. The module system as claimed in claim 1, further comprising:
   a housing, the basic module and/or the expansion module being able to be arranged in the housing.

6. The module system as claimed in claim 1, wherein the basic module has a basic module range of functions, the number of functional groups supplementing and/or expanding the basic module range of functions.

7. The module system as claimed in claim 1, wherein the expansion module interface, the control device interface and/or the basic module interface include a safety limitation circuit.

8. The module system as claimed in claim 1, wherein the energy provided via the energy supply interface is used to supply energy to the expansion module interface.

9. The module system as claimed in claim 1, wherein the basic module and the expansion module are housed in a same housing.

10. The module system as claimed in claim 9, wherein the control device is external to the same housing.

11. The module system as claimed in claim 1, wherein the control device is external to the same housing.

\* \* \* \* \*